(12) United States Patent
Chaturvedi

(10) Patent No.: US 8,044,029 B2
(45) Date of Patent: Oct. 25, 2011

(54) SULFATIDES FOR TREATMENT OF AUTOIMMUNE DISORDERS

(75) Inventor: Vipin Kumar Chaturvedi, Rancho Santa Fe, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 0 days.

(21) Appl. No.: 11/529,793

(22) Filed: Sep. 28, 2006

(65) Prior Publication Data

US 2007/0087979 A1 Apr. 19, 2007

Related U.S. Application Data

(60) Provisional application No. 60/722,184, filed on Sep. 29, 2005.

(51) Int. Cl.
*A61K 31/7032* (2006.01)
(52) U.S. Cl. .......................... 514/25; 536/17.6
(58) Field of Classification Search .............. 514/25; 536/17.6
See application file for complete search history.

(56) References Cited

U.S. PATENT DOCUMENTS

| 5,486,536 | A | * | 1/1996 | Ward et al. ............... 514/460 |
| 5,565,433 | A | * | 10/1996 | Banville et al. ............. 514/25 |
| 5,674,690 | A | * | 10/1997 | Kolodny et al. ............ 435/7.1 |
| 6,352,831 | B1 | * | 3/2002 | Buschard et al. ........... 435/7.1 |

FOREIGN PATENT DOCUMENTS

EP   0 717 995 A2   6/1996

OTHER PUBLICATIONS

Definition of symptom, Merriam-Webster Medical Dictionary, http://www2.merriam-webster.com, accessed online on Jul. 15, 2008.*
Marbois et al. Biochimica et Biophysica Acta, 2000, 1484, p. 59-70.*
Duran et al. Brain, 1999, 122, p. 2297-2307.*
Definition of prevent, Oxford English Dictionary, http://dictionary.oed.com/, accessed online on May 27, 2010.*
Compostella et al. Tetrahedron, 2002, 58, p. 8703-8708.*
Shamshiev et al. J. Exp. Med. 2002, 195(8), p. 1013-1021.*
Entry for Autoimmune disorders, PubMed Health, http://www.ncbi.nlm.nih.gov/pubmedhealth/PMH0001819/, accessed online on Jul. 14, 2011.*
Gold et al. Molecular Medicine Today, 2000, 6, p. 88-91.*
Zou et al. Neuropharmacology, 2002, 42, p. 731-739.*
Buschard et al. (2005) Involvement of sulfatide in beta cells and type 1 and type 2 diabetes. Diabetologia 48:1957-1962.
Hsu et al. (1998) Electrospray ionization tandem mass spectrometric analysis of sulfatide. Determination of fragmentation patterns and characterization of molecular species expressed in brain and in pancreatic islets. Biochimica et Biophysica Acta 1392 202-216.
Steinman, Lawrence and Scott S. Zamvil. "Virtues and Pitfalls of EAE for the Development of Therapies for Multiple Sclerosis." Trends in Immunology. 26.11 (2005): 565-571.
Mix, Eilhard, et al. "Animal Models of Multiple Sclerosis for the Development and Validation of Novel Therapies—Potential and Limitations." Journal of Neurology. 255 (Supp 6) (2008): 7-14.
Lassmann, Hans. "Chronic Relapsing Experimental Allergic Encephalomyelitis: Its value as an Experimental Model for Multiple Sclerosis." Journal of Neurology. 229 (1983): 207-220.
Abreu, Sergio L., et al. "Interferon in Experimental Autoimmune Encephalomyelitis: Intraventricular Administration." Journal of Interferon Research. 6 (1986): 627-632.
Steinman, Lawrence, MD and Scott S. Zamvil. "How to Successfully Apply Animal Studies in Experimental Allergic Encephalomyelitis to Research on Multiple Sclerosis." American Neurological Association. 60.12 (2006): 12-21.
Jahng, Alex, et al. "Prevention of Autoimmunity by Targeting a Distinct, Noninvariant CD1d-reactive T Cell Population Reactive to Sulfatide." Journal of Experimental Medicine. 199.7 (2004): 947-957.
Halder, Ramesh C., et al. "Type II NKT Cell-Mediated Anergy Induction in Type I NKT Cells Prevents Inflammatory Liver Disease." The Journal of Clinical Investigation. 117.8 (2007): 2302-2312.
Zajonc, Dirk M., et al. "Structural Basis for CD1d Presentation of a Sulfatide Derived from Myelin and Its Implications for Autoimmunity." The Journal of Experimental Medicine. 202.11 (2005): 1517-1526.
Abreu, Sergio L. "Suppression of Experimental Allergic Encephalomyelitis by Interferon." Immunological Communications. 11.1 (1982): 1-7.
Bolton, C. "The Translation of Drug Efficacy from In Vivo Models to Human Disease with Special Reference to Experimental Autoimmune Encephalomyelitis and Multiple Sclerosis." Inflammopharmacology 15 (2007): 183-187.
Lublin, Fred D. "Relapsing Experimental Allergic Encephalomyelitis: An Autoimmune Model of Multiple Sclerosis." Springer Seminars in Immunopathology. 8 (1985): 197-208.
Yednock, Ted A., et al, "Prevention of Experimental Autoimmune Encephalomyelitis by Antibodies Against a4bl Integrin." Nature. 365 (1992): 63-66.
Gold, Ralf, et al. "Understanding Pathogenesis and Therapy of Multiple Sclerosis Via Animal Models: 70 Years of Merits and Culprits in Experimental Autoimmune Encephalomyelitis Research." Brain. 129 (2006): 1953-1971.
Teitelbaum, Dvora, et al. "Immunomodulation of Experimental Autoimmune Encephalomyelitis by Oral Administration of Copolymer 1." Proceedings of the National Academy of Sciences. 96 (1999): 3842-3847.

(Continued)

*Primary Examiner* — Shaojia Anna Jiang
*Assistant Examiner* — Jonathan S Lau
(74) *Attorney, Agent, or Firm* — Knobbe Martens Olson & Bear LLP

(57) ABSTRACT

Disclosed herein are methods for the treatment of autoimmune or immune related diseases or disorders. Also disclosed are methods for treating such autoimmune or immune related diseases or disorders with the administration of sulfatides. Also disclosed herein are methods of treating autoimmune or immune related diseases or disorders by administering an amount of a sulfatide to the body of a patient effective to reduce or prevent the symptoms of the autoimmune or immune related disease or disorder.

3 Claims, 9 Drawing Sheets

OTHER PUBLICATIONS

Brossay, Laurent and Mitchell Kronenberg. "Highly Conserved Antigen-Presenting Function of CD1d Molecules." Immunogenetics. 50 (1999): 146-151.

Kashiwase, Koichi. "The CD1d Natural Killer T-cell Antigen Presentation Pathway is Highly Conserved Between Humans and Rhesus Macaques." Immunogenetics. 54 (2003): 776-781.

* cited by examiner

Days after MOG35-55 immunization: Days after the disease induction in C57.BL/6J mice
Control: Mice treated with vehicle/PBS only
Sulfatide: Mice treated with sulfatide (20μg/mouse)

Days after PLP139-151 immunization: Days after the disease induction in SJL/J mice
Control: Mice treated with vehicle/PBS only
Sulfatide: Mice treated with sulfatide (20μg/mouse)

Days after PLP139-151 immunization Days after the disease induction in SJL/J mice
Control: Mice treated with vehicle/PBS only
Cis-tetracosenoyl: Mice treated with cis-tetracosenoyl sulfatide (20μg/mouse)

Age in weeks: NOD mice age
Sulfatide female: Female NOD mice treated with sulfatide
Sulfatide male: Male NOD mice treated with sulfatide
Control lipid female: Female NOD mice treated with Mono GM1
Control lipid male: Male NOD mice treated with Mono GM1

SERUM ALT AND AST

ALT: Alanine amino transferase
AST: Aspartate amino transferase

Mice: C57BL/6 female
Con A : Concanavalin A; 8.5 mg/kg/animal
Sulfatide: 1 mg/kg/animal

Mice: C57BL/6 female
Con A : Concanavalin A; 8.5 mg/kg/animal
Sulfatide: 1 mg/kg/animal

None: No sulfatide treatment
Day -1: Sulfatide treated, one day before infection
Day 0: Sulfatide treated, same day as infection
Day +1: Sulfatide treated, one day postinfection
Day +28: Sulfatide treated, four weeks postinfection
Infection: HIV-1 virus infection
Replication: HIV-1 virus replication None: No sulfatide treatment
Day -1: Sulfatide treated one day before infection
No infection/No treatment: No HIV-1 infection and no sulfatide treatment
Myeloid: lineage
Erythroid: lineage
Megakaryoid: lineage

SULFATIDES FOR TREATMENT OF AUTOIMMUNE DISORDERS

CROSS-REFERENCE TO RELATED APPLICATIONS

This application claims priority under 35 U.S.C. §119(e) to U.S. Provisional Application No. 60/722,184 filed Sep. 29, 2005, which is hereby incorporated by reference in its entirety.

BACKGROUND OF THE INVENTION

1. Field of the Invention

The present embodiments relate to methods for the treatment of autoimmune or immune related diseases or disorders. More specifically the present embodiments relate to sulfatides for use in the treatment of autoimmune or immune related diseases or disorders.

2. Description of the Related Art

Autoimmune diseases effect millions of people worldwide and can have devastating effects on lifespan and quality of life. Despite advances in medical science, many autoimmune diseases have evaded treatment because the mechanisms of disease are complex and poorly understood. Also, unlike most diseases where treatment involves working with the body's immune system to combat a foreign invader, in autoimmune diseases, the immune system itself is exacerbating the problem. This makes any treatment much more difficult because it must address the immune response directly to combat the problem.

In multiple sclerosis, for example, the immune system pathologically recognizes some self-antigens from myelin membranes as foreign and initiates an immune response against them. This results in demyelination, the destructive removal of myelin which is an insulating and protective fatty protein that sheaths nerve cells (neurons). The demyelination in multiple sclerosis is mediated by a T-cell guided immune response that is either initiated from antigen-presenting events in the CNS or induced following the peripheral activation by a systemic molecular mimicry response.

Experimental autoimmune encephalomyelitis (EAE) is a prototypic T-cell mediated autoimmune disease, characterized by inflammation and demyelination in the central nervous system accompanied by paralysis following immunization with myelin antigens, for example, myelin basic protein (MBP), myelin oligodendrocyte glycoprotein (MOG) or proteolipid protein (PLP). EAE shares many pathological and immune dysfunctions with human MS and is a widely accepted model for studying human MS.

Glycolipids can be recognized by T cells in the context of class I MHC-like cell surface proteins known as CD1. Myelin is a rich source of glycolipids, and myelin is the target of an autoimmune process during EAE in which the influence of myelin-derived lipids and their presentation to T cells in the CNS can be easily studied. In order to derive effective treatments for multiple sclerosis, further characterization of glycolipid-reactive T cells is needed. Sulfatide is one of the major glycolipids in myelin and has been shown to bind to CD1d. (Jahng, et al. J. Exp. Med. Vol. 199 Num. 7: 947-957, 2004.)

In AIDS, T-cells are systematically depleted by the HIV virus. Like with many autoimmune diseases, the immune system itself tends to advance the disease because the virus is spread through immune cells. Human immunodeficiency virus (HIV) infects CD4+ cells in conjunction with a cellular coreceptor, CXCR4, or CCR5/CCR3. HIV infection of human cells results in loss of CD4+ T lymphocytes as the virus undergoes rapid replication generating mutations in its envelope region of the viral genome. These also include drug resistant mutants as the infected individuals are treated with antiretroviral drugs including zidovudine (AZT), nucleoside reverse transcriptase inhibitor (NRTI), or a non-nucleoside reverse transcriptase inhibitor (NNRTI), and protease inhibitor. Further, there is an exhaustion of the cytotoxic T lymphocytes and the eventual failure of the immune system, both cell mediated and humoral responses, of the infected individual to fight the infection arising from the generation of multiple HIV strains in vivo. The immune system is also exacerbated due to opportunistic infections of the infected individuals that are immune compromised.

The severe combined immunodeficiency mouse transplanted with human fetal thymus and liver tissues (SCID-hu Thy/Liv) is a small animal model that mimics HIV infection in humans both in terms of loss of CD4+ T lymphocytes and high viral replication. The system also enables testing in the laboratory of various drugs to combat HIV infection in vivo in a convenient model system in the absence of confounding factors found in humans. Thus, this system is a useful model for preclinical testing of anti-HIV drugs in vivo prior to undertaking clinical trials in infected humans.

Cytopenia, particularly thrombocytopenia are a major risk factor in HIV infection, heart disease, and cancer. Hematopoietic abnormalities can cause or lead to multiple cytopenia in HIV infected individuals with thrombocytopenia emerging as a major risk factor for morbidity and mortality and even more so in patients also suffering from heart conditions.

Concanavalin A (Con A)-induced hepatitis in the mouse is a well-characterized model of T cell-mediated liver diseases. This model has been extensively used as an excellent model mimicking human T cell-mediated liver diseases, such as autoimmune hepatitis ((Tiegs et al., 1992, JCI, Mizuhara H., JEM, 1994, Toyabe S, JI, 1997). A single injection of Con A is sufficient for the T cell-mediated liver injury in mice (Tiegs et al., 1992, JCI, Mizuhara H., JEM, 1994, Toyabe S, JI, 1997). Serum enzymes and histological evidence of Con A induced hepatitis is observed following 8-24 hours, as shown by elevated serum levels of ALT and AST and the occurrence of histological evidence of hepatic lesions characterized by a massive granulocytes accumulation, CD4$^+$ T cell infiltration and an influx of a relatively small number of CD8$^+$ T cells and hepatocyte necrosis/apoptosis (Tiegs et al., 1992, JCI, Mizuhara H., JEM, 1994, Schumann J., 2000, Am. J. Pathol., Chen et al., 2001). Recently, several investigators have implicated hepatic NKT cells in the development of Con A-induced hepatitis. Both Jα18 and CD1d-deficient mice that lack NKT cells are resistant to Con A-induced hepatic injury (Kaneko et al., 2000; Takeda et al., 2000), indicating that classical CD1d-restricted NKT cells that express the iNKT cell receptor are critically involved in the process of Con A induced hepatic injury.

SUMMARY OF THE INVENTION

One embodiment relates to a method of treating a patient with symptoms of an autoimmune disease including administering an amount of a sulfatide effective to reduce said symptoms, wherein the autoimmune disease is not multiple sclerosis.

In one aspect of the embodiment, the sulfatide can have following chemical structure:

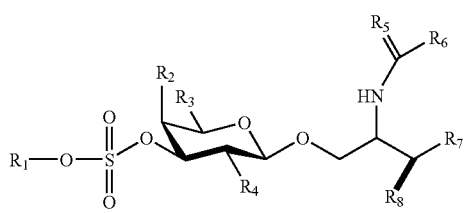

wherein $R_1$ is selected from the group consisting of a bond, a hydrogen, a $C_1$ to $C_{30}$ alkyl, $C_1$ to $C_{30}$ substituted alkyl, a $C_1$ to $C_{30}$ alkenyl, a $C_1$ to $C_{30}$ substituted alkenyl and a $C_5$ to $C_{12}$ sugar; $R_2$ is selected from the group consisting of a hydrogen, a hydroxy group, a methoxy group, and an alkoxy group; $R_3$ is selected from the group consisting of a hydrogen, a hydroxy group, a methoxy group, an ethoxy group, and an alkoxy group; $R_4$ is selected from the group consisting of a hydrogen, a hydroxy group and an alkoxy group; $R_5$ is selected from the group consisting of a hydrogen, a hydroxyl, a carbonyl, an alkoxy and a bond; $R_6$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; R7 is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_8$ is selected from the group consisting of a hydrogen, a hydroxyl group, a carbonyl, an alkoxy group and a bond.

In another aspect, the sulfatide has following chemical structure:

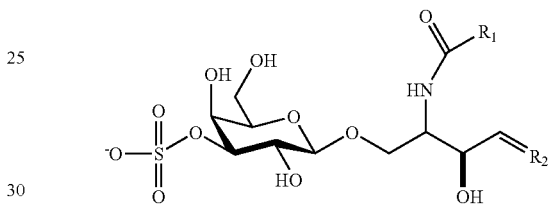

wherein $R_1$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_2$ is selected from the group consisting of a hydrogen, a hydroxyl group, a carbonyl, an alkoxy group and a bond.

In another aspect, the sulfatide can have the following chemical structure:

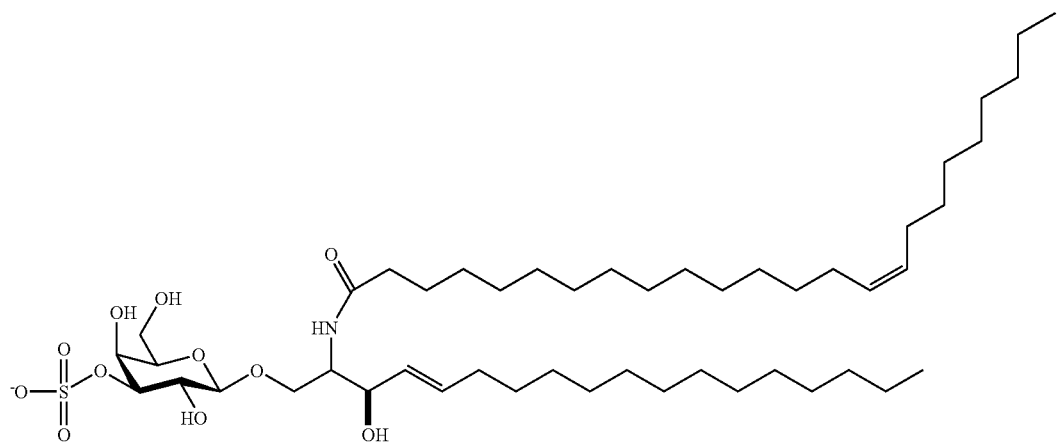

In yet another aspect, the sulfatide is: (2S, 3R, 4E)-N-nervonic-1-[-D-(3-sulfate)-galactopyranosyl]-2-amino-octa-decene-3-ol.

In still another aspect, the autoimmune disease can be, for example, systemic lupus erythematsosus, AIDS, Alzheimer's disease, rheumatoid arthritis, insulin dependent diabetes mellitus, autoimmune hepatitis, asthma or celiac disease.

In another aspect, the sulfatide can be administered by one or more of the following routes: intravenous, intraperitoneal, inhalation, intramuscular, subcutaneous and oral.

Another embodiment relates to a method of treating a patient with symptoms of an autoimmune disease comprising administering an amount of a sulfatide effective to reduce said symptoms, wherein the sulfatide has the following chemical structure:

a hydroxy group, a methoxy group, and an alkoxy group; $R_3$ is selected from the group consisting of a hydrogen, a hydroxy group, a methoxy group, an ethoxy group, and an alkoxy group; $R_4$ is selected from the group consisting of a hydrogen, a hydroxy group and an alkoxy group; $R_5$ is selected from the group consisting of a hydrogen, a hydroxyl, a carbonyl, an alkoxy and a bond; $R_6$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; R7 is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_8$ is selected from the group consisting of a hydrogen, a hydroxyl group, a carbonyl, an alkoxy group and a bond.

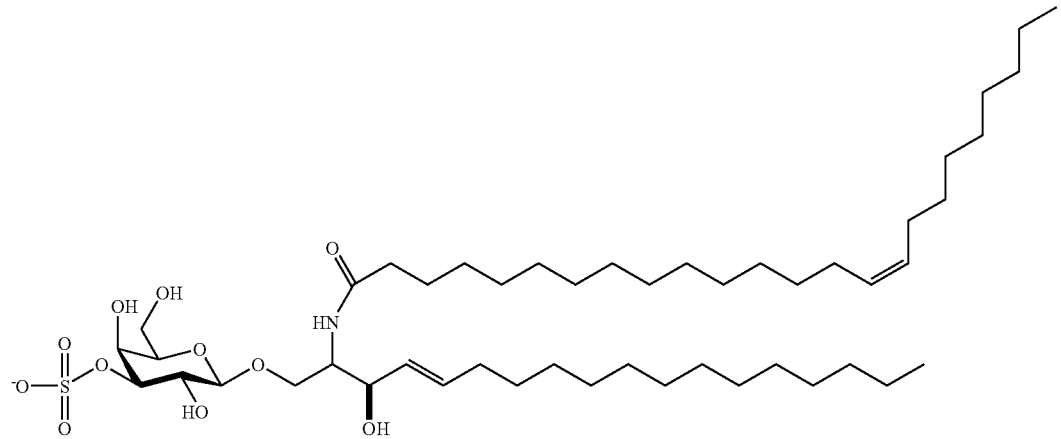

In one aspect, the autoimmune disease can be, for example, multiple sclerosis, systemic lupus erythematsosus, AIDS, Alzheimer's disease, rheumatoid arthritis, insulin dependent diabetes mellitus, autoimmune hepatitis, asthma or celiac disease.

In another aspect, the autoimmune disease is multiple sclerosis.

Another embodiment relates to a method of treating the indications of an autoimmune disease in a patient comprising administering to said patient a therapeutically effective amount of a sulfatide, wherein the autoimmune disease is not multiple sclerosis.

In one aspect, the sulfatide has following chemical structure:

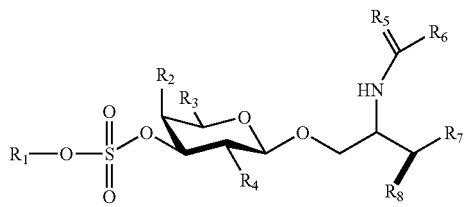

wherein $R_1$ is selected from the group consisting of a bond, a hydrogen, a $C_1$ to $C_{30}$ alkyl, $C_1$ to $C_{30}$ substituted alky, a $C_1$ to $C_{30}$ alkenyl, a $C_1$ to $C_{30}$ substituted alkenyl and a $C_5$ to $C_{12}$ sugar; $R_2$ is selected from the group consisting of a hydrogen, In another aspect, the sulfatide has the following chemical structure:

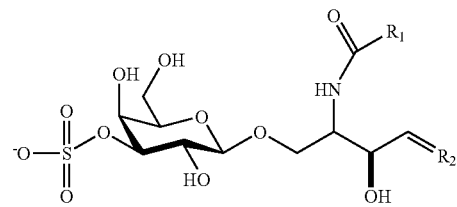

wherein $R_1$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_2$ is selected from the group consisting of a hydrogen, a hydroxyl group, a carbonyl, an alkoxy group and a bond.

In another aspect, the sulfatide is (2S, 3R, 4E)-N-nervonic-1-[-D-(3-sulfate)-galactopyranosyl]-2-amino-octadecene-3-ol.

In yet another aspect, the sulfatide has the following chemical structure:

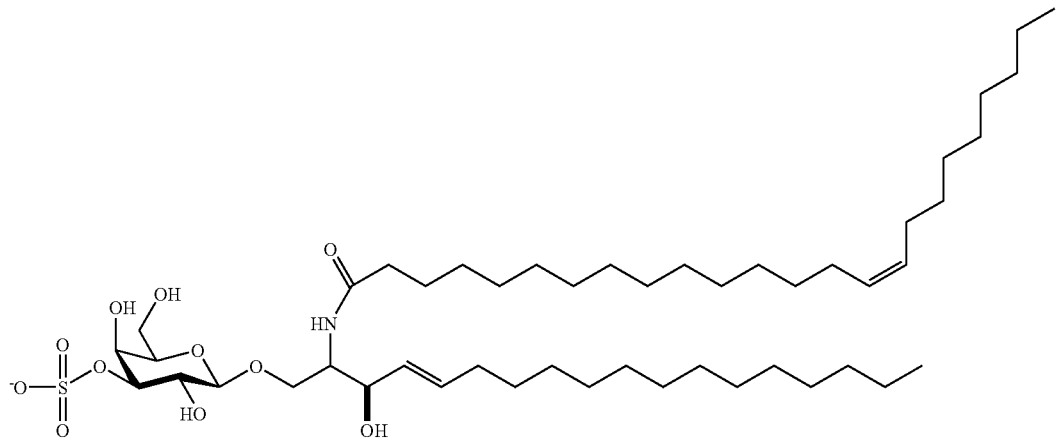

In yet another aspect, the autoimmune disease can be, for example, systemic lupus erythematsosus, AIDS, Alzheimer's disease, rheumatoid arthritis, insulin dependent diabetes mellitus, autoimmune hepatitis, asthma or celiac disease.

In still another aspect, the autoimmune disease can be multiple sclerosis.

In another aspect, the autoimmune disease is AIDS.

In another aspect, the sulfatide can be administered by one or more of the following routes: intravenous, intraperitoneal, inhalation, intramuscular, subcutaneous and oral.

Another embodiment relates to a method of treating or preventing the symptoms of an autoimmune disease in a mammal, comprising the step of administering to said mammal a therapeutically effective amount of a sulfatide formulated in a pharmaceutically acceptable vehicle, wherein the autoimmune disease is not multiple sclerosis.

In one aspect, the mammal is a human.

In another aspect, the sulfatide has following chemical structure:

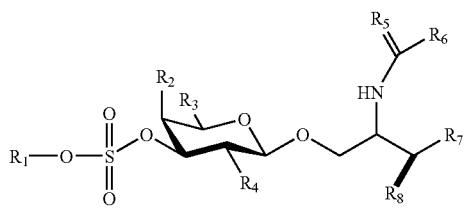

wherein $R_1$ is selected from the group consisting of a bond, a hydrogen, a $C_1$ to $C_{30}$ alkyl, $C_1$ to $C_{30}$ substituted alkyl, a $C_1$ to $C_{30}$ alkenyl, a $C_1$ to $C_{30}$ substituted alkenyl and a $C_5$ to $C_{12}$ sugar; $R_2$ is selected from the group consisting of a hydrogen, a hydroxy group, a methoxy group, and an alkoxy group; $R_3$ is selected from the group consisting of a hydrogen, a hydroxy group, a methoxy group, an ethoxy group, and an alkoxy group; $R_4$ is selected from the group consisting of a hydrogen, a hydroxy group and an alkoxy group; $R_5$ is selected from the group consisting of a hydrogen, a hydroxyl, a carbonyl, an alkoxy and a bond; $R_6$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; R7 is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_8$ is selected from the group consisting of a hydrogen, a hydroxyl group, a carbonyl, an alkoxy group and a bond.

In yet another aspect, the sulfatide has following chemical structure:

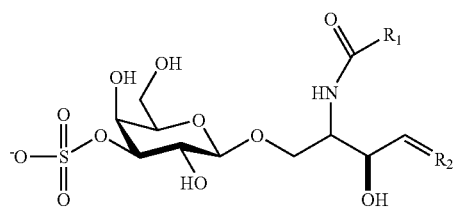

wherein $R_1$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_2$ is selected from the group consisting of a hydrogen, a hydroxyl group, a carbonyl, an alkoxy group and a bond.

In still another aspect, the sulfatide is (2S, 3R, 4E)-N-nervonic-1-[-D-(3-sulfate)-galactopyranosyl]-2-amino-octadecene-3-ol.

In another aspect, the sulfatide has the following chemical formula:

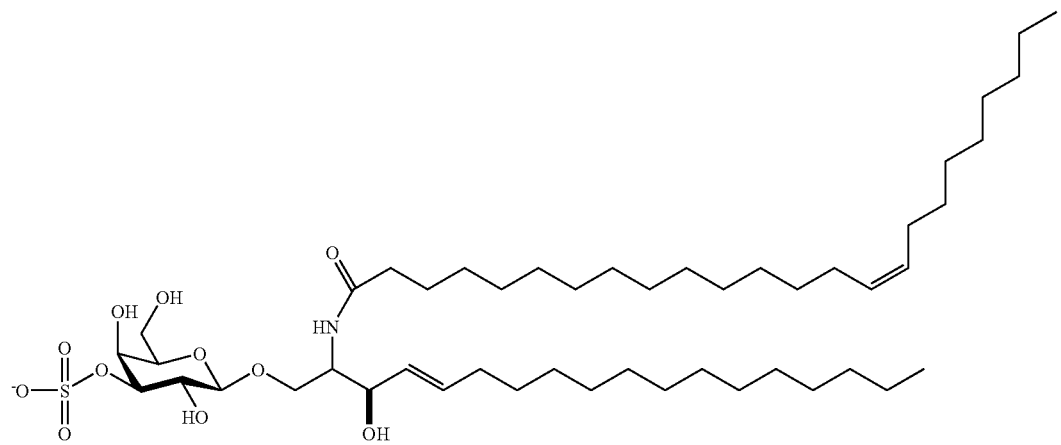

DETAILED DESCRIPTION OF THE INVENTION

Figure 1:
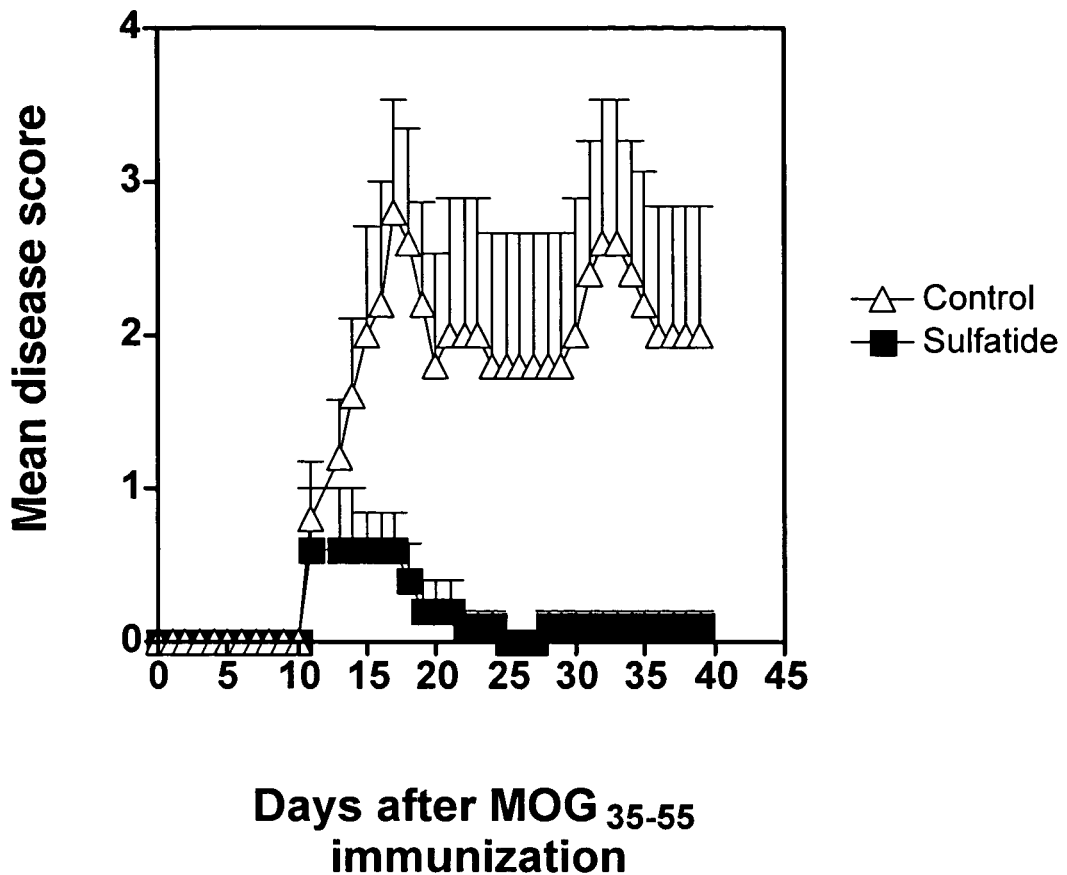
FIG. 1 shows that treatment of mice with sulfatide reverses ongoing chronic EAE in C57.BL/6J mice. Mice were injected intraperitoneally with 20 μg of bovine brain sulfatide (■) or with PBS/vehicle alone (Δ) at the onset of disease (↑).

The present embodiments are related to treatments for a wide variety of autoimmune or immune related diseases or disorders including, for example, multiple sclerosis, systemic lupus erythematsosus, AIDS, Alzheimer's disease, rheumatoid arthritis, insulin dependent diabetes mellitus, autoimmune hepatitis, asthma, and celiac disease.

Some embodiments relate to methods for treating such autoimmune or immune related diseases or disorders with the administration of sulfatides. More specifically, some embodiments relate to methods of treating autoimmune or immune related diseases or disorders by administering an amount of a sulfatide to the body of a patient effective to reduce or prevent the symptoms of the autoimmune or immune related disease or disorder. In preferred embodiments the sulfatide has the following chemical formula I:

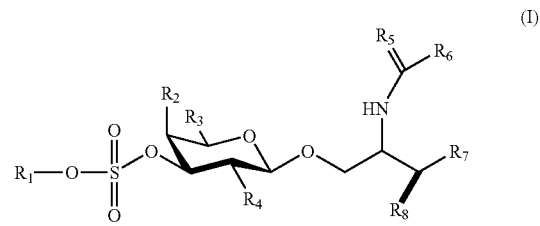

(I)

wherein $R_1$ can be a bond, a hydrogen, a $C_1$ to $C_{30}$ alkyl, a $C_1$ to $C_{30}$ substituted alkyl, a $C_1$ to $C_{30}$ alkenyl, a $C_1$ to $C_{30}$ substituted alkenyl or a $C_5$ to $C_{12}$ sugar; $R_2$ can be a hydrogen, a hydroxy group, a methoxy group, or an alkoxy group; $R_3$ can be a hydrogen, a hydroxy group, a methoxy group, an ethoxy group, or an alkoxy group; $R_4$ can be a hydrogen, a hydroxy group or an alkoxy group; $R_5$ can be a hydrogen, a hydroxy group, a carbonyl, an alkoxy group or a bond; $R_6$ can be a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl, or a $C_1$ to $C_{40}$ alkynl; R7 can be a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl, or a $C_1$ to $C_{40}$ alkynl; and R8 can be a hydrogen, a hydroxy group, a carbonyl, an alkoxy group or a bond.

In other embodiments, the sulfatide has the following chemical formula II:

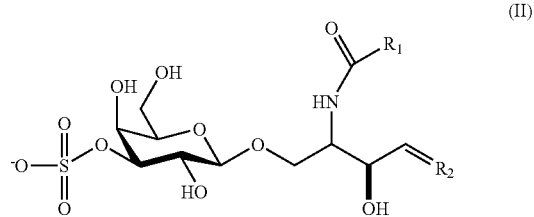

(II)

$R_1$ is selected from the group consisting of a $C_1$ to $C_{40}$ alkyl, a $C_1$ to $C_{40}$ substituted alkyl, a $C_1$ to $C_{40}$ alkenyl, a $C_1$ to $C_{40}$ substituted alkenyl and a $C_1$ to $C_{40}$ alkynl; and $R_2$ is selected from the group consisting of a hydrogen, a hydroxyl group, a carbonyl, an alkoxy group and a bond.

As used herein, the term "alkyl" means any unbranched or branched, saturated hydrocarbon. The term "substituted alkyl" means any unbranched or branched, substituted saturated hydrocarbon. Cyclic compounds, both cyclic hydrocarbons and cyclic compounds having heteroatoms, are within the meaning of "alkyl."

As used herein, the term "substituted" means any substitution of a hydrogen atom with a functional group.

As used herein, the term "functional group" has its common definition, and refers to chemical moieties preferably selected from the group consisting of a halogen atom, $C_1$-$C_{20}$ alkyl, substituted $C_1$-$C_{20}$ alkyl, perhalogenated alkyl, cyloalkyl, substituted cycloalkyl, aryl, substituted aryl, benzyl, hetroaryl, substituted heteroaryl, cyano, and nitro.

As used herein, the terms "halogen" and "halogen atom" refer to any one of the radio-stable atoms of column 17 of the Periodic Table of the Elements, preferably fluorine, chlorine, bromine, or iodine, with fluorine and chlorine being particularly preferred.

As used herein, the term "alkenyl" means any unbranched or branched, substituted or unsubstituted, unsaturated hydrocarbon. The term "substituted alkenyl" means any unbranched or branched, substituted unsaturated hydrocarbon, substituted with one or more functional groups, with unbranched $C_2$-$C_6$ alkenyl secondary amines, substituted $C_2$-$C_6$ secondary alkenyl amines, and unbranched $C_2$-$C_6$ alkenyl tertiary amines being within the definition of "substituted alkyl." Cyclic compounds, both unsaturated cyclic hydrocarbons and cyclic compounds having heteroatoms, are within the meaning of "alkenyl."

As used herein, the term "alkoxy" refers to any unbranched, or branched, substituted or unsubstituted, saturated or unsaturated ether.

As used herein, the term "sulfatide" retains its general accustomed meaning and refers to a cerebroside sulfuric ester containing one or more sulfate groups in the sugar portion of the molecule.

As used herein, the term "cerebroside" refers to any lipid compound containing a sugar, and generally of the type normally found in the brain and nerve tissue.

The compounds of formula (I), (II) and (III) may be in the form of pharmaceutically acceptable nontoxic salts thereof. Salts of formula (I), (II) and (III) include acid added salts, such as salts with inorganic acids (e.g., hydrochloric acid, sulfuric acid, nitric acid and phosphoric acid) or with organic acids (e.g., acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid).

The compounds of formula (I), (II) and (III) may be in the form of solvates thereof (e.g., hydrates).

The compounds of formula (I), (II) and (III) can be produced by any purposive method to synthesize sulfatides.

The compounds of formulas (I), (II) and (III) can also be isolated from natural products (e.g., biological organisms) and purified by column chromatography or the like.

In one embodiment, the sulfatide has the chemical formula: (2S, 3R, 4E)-N-nervonic-1-[-D-(3-sulfate)-galactopyranosyl]-2-amino-octadecene-3-ol. This chemical formula is also referred to as cis-tetracosenoyl sulfatide.

In another embodiment, the sulfatide has the following chemical structure:

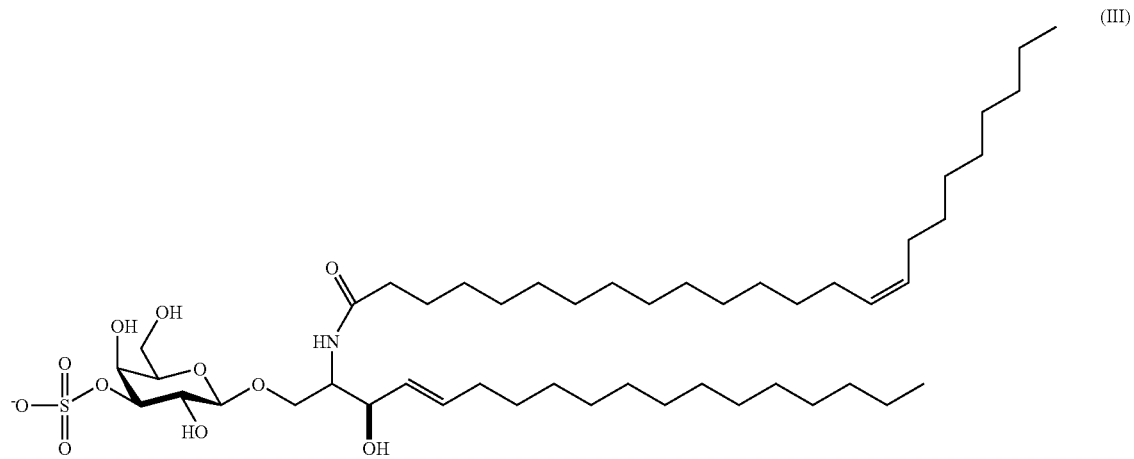

(III)

In some embodiments, the sulfatide can be, for example, bovine brain-derived sulfatide which is a mixture of about 20 different species obtained from Sigma Inc. (Chicago, Ill., USA). In other embodiments, the sulfatide is semisynthetic and is a single species of sulfatide, for example, cis-tetracosenoyl sulfatide or lysosulfatide obtained from Maitreya Inc, (Pleasant Gap, Pa., USA). In still other embodiments, the sulfatide can be a totally synthetic sulfatide.

Another embodiment is related to a method of treating the various indications of autoimmune or immune related diseases or disorders. In particular, one aspect of the present embodiment is related to a method of treating a patient suffering from symptoms of an autoimmune or immune related disease or disorder, such as, for example, multiple sclerosis, systemic lupus erythematsosus, AIDS, Alzheimer's disease, rheumatoid arthritis, insulin dependent diabetes mellitus, autoimmune hepatitis, asthma, and celiac disease.

Some embodiments relate to a method of treating asthma in a patient. Bronchial asthma is associated with an inflammatory process in the lungs that is characterized by the presence in the airways of large numbers of cytokines-secreting CD4+ T cells. CD4 antigen is expressed not only by class II major histocompatibility complex (MHC)-restricted CD4+ T cells, but also by CD1-restricted NK T cells. These cells can be categorized into 2 subsets based on those using invariant receptors, such as invariant NK T cells ("iNK T cells") and those using variable receptors, such as non-invariant NK T cells ("non-iNK T cells"). Mouse models of allergic asthma have shown that NK T cells are required for the development of allergen-induced airway hyperreactivity.

Studies have also shown that a major percentage of the pulmonary CD4+ CD3+ cells in patients with moderate-to-severe persistent asthma were iNK T cells. However, this was not the case in the lungs of patients with sarcoidosis. Since these iNK T cells constitute only a minor population (around 0.1%) of the CD4+ T cells in peripheral blood, their large number in lungs of asthmatic patients suggest their selective enrichment. It has been shown that iNK T cells can recognize the synthetic glycolipid α-galactosyl-ceramide, the self-glycolipid isoglobotrihexosyl-ceramide (iGb3), bacterial glycosphingolipids and glycolipids from plant pollens. A subset of non-iNK T cells also recognizes self-glycolipid sulfatide as well as other sulfatides and glycolipids of the present embodiments. One example of the mechanisms by which sulfatide controls autoimmunity involves the inactivation or non-responsiveness of iNK T cells, hence in some embodiments, sulfatide can be used to treat asthma in a patient.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively.

In some other embodiments, the sulfatide can be administered alone or in combination with another therapeutic compound. Any currently known therapeutic compound used in treatment of the target autoimmune disease can be used. In one preferred embodiment, no adjuvant is used.

Many different modes and methods of administration of the sulfatide are contemplated. In some embodiments, delivery routes include, for example, intravenous, intraperitoneal, inhalation, intramuscular, subcutaneous, and oral administration or any other delivery route known in the art. Depending on the particular administration route, the dosage form may be, for example, solid, semisolid, liquid, vapor or aerosol preparation. The dosage form may include, for example, those additives, lubricants, stabilizers, buffers, coatings, and excipients as is standard in the art of pharmaceutical formulations Many pharmaceutical formulations are contemplated. In some embodiments, the pharmaceutical formulations can be prepared by conventional methods using the following pharmaceutically acceptable vehicles or the like: excipients such as solvents (e.g., water, physiological saline), bulking agents and filling agents (e.g., lactose, starch, crystalline cellulose, mannitol, maltose, calcium hydrogenphosphate, soft silicic acid anhydride and calcium carbonate); auxiliaries such as solubilizing agents (e.g., ethanol and polysolvates), binding agents (e.g., starch, polyvinyl pyrrolidine, hydroxypropyl cellulose, ethylcellulose, carboxymethyl cellulose and gum arabic), disintegrating agents (e.g., starch and carboxymethyl cellulose calcium), lubricating agents (e.g., magnesium stearate, talc and hydrogenated oil), stabilizing agents (e.g., lactose, mannitol, maltose, polysolvates, macrogol, and polyoxyethylene hydrogenated castor oil), isotonic agents, wetting agents, lubricating agents, dispersing agents, buffering agents and solubilizing agents; and additives such as antioxidants, preservatives, flavoring and aromatizing agents, analgesic agents, stabilizing agents, coloring agents and sweetening agents.

If necessary, glycerol, dimethyacetamide, 70% sodium lactate, surfactants and alkaline substances (e.g., ethylenediamine, ethanol amine, sodium carbonate, arginine, meglumine and trisaminomethane) can also be added to various pharmaceutical formulations.

In the context of some embodiments, the dosage form can be that for oral administration. Oral dosage compositions for small intestinal delivery include, for example, solid capsules as well as liquid compositions which contain aqueous buffering agents that prevent the sulfatide or other ingredients from being significantly inactivated by gastric fluids in the stomach, thereby allowing the sulfatide to reach the small intestines. Examples of such aqueous buffering agents which can be employed in the present embodiments include, for example, bicarbonate buffer at a pH of from about 5.5 to about 8.7. Tablets can also be made gastroresistent by the addition of, e.g., cellulose acetate phthalate or cellulose acetate terephthalate.

In some embodiments, the specific amount of sulfatide administered to a patient will vary depending upon the disease or condition being treated, as well as the age, weight and sex of the patient being treated. Generally, to achieve such a final concentration in, e.g., the intestines or blood, the amount of sulfatide molecule in a single dosage composition of the present embodiments will generally be about 0.1 milligrams to about 100 milligrams, preferably about 2.0 milligrams to about 60 milligrams, more preferably about 20 milligrams to about 50 milligrams. Likewise, the amount of a secondary therapeutic compound in a single oral dosage composition of the present embodiments will generally be in the range of about 0.01 milligrams to about 1000 milligrams, more preferably about 0.1 milligrams to about 100 milligrams. Obviously, the exact dosage will vary with the disease or disorder being treated, the preferred ranges being readily determinable.

In another embodiment, the sulfatide can be combined with a pharmaceutically acceptable vehicle. Suitable pharmaceutically acceptable vehicles include, for example, phosphate buffered saline and PBS-tween. In one embodiment, 0.1-10 mg/kg body weight of sulfatide are administered to the patient. More preferably, 1-10 mg/kg body weight of sulfatide are administered. Preferably, this dosage is repeated each day as needed. Alternative dosages and dose schedules are discussed infra.

In the present embodiments, sulfatides can be administered to a patient suffering from autoimmune diseases to improve the patient's condition. Accordingly, patients suffering from one or more of the various indications of a autoimmune or immune related diseases and disorders such as multiple sclerosis, systemic lupus erythematsosus, AIDS, Alzheimer's disease, rheumatoid arthritis, insulin dependent diabetes mellitus, autoimmune hepatitis, asthma and celiac disease can be treated using sulfatides according to the present embodiments.

In accordance with the embodiments, sulfatides can be administered to alleviate a patient's symptoms, or can be administered to counteract a mechanism of the disorder itself. It will be appreciated by those of skill in the art that these treatment purposes are often related and that treatments can be tailored for particular patients based on various factors. These factors can include the age, gender, or health of the patient, and the progression of autoimmune or immune related disease or disorder. The treatment methodology for a patient can be tailored accordingly for dosage, timing of administration, route of administration, and by concurrent or sequential administration of other therapies.

In one exemplary embodiment, an 70 kg adult patient at risk of chemical liver damage from prescription drugs or drugs of abuse is given a daily i.m. injection of 70 mg sulfatide in 1.0 ml phosphate buffered saline to treat liver damage. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat AIDS. This dosage can be adjusted based on the results of the treatment and the judgment of the attending physician. Treatment is preferably continued for at least about 1 or 2 weeks, preferably at least about 1 or 2 months, and may be continued on a chronic basis.

In yet another exemplary embodiment, an 70 kg adult human is given a daily i.m. injection of 70 mg sulfatide in 1.0 ml phosphate buffered saline to treat multiple sclerosis. This dosage can be adjusted based on the results of the treatment and the judgment of the attending physician. Treatment is preferably continued for at least about 1 or 2 weeks, preferably at least about 1 or 2 months, and may be continued on a chronic basis.

In still another exemplary embodiment, an 70 kg adult human is given a daily i.m. injection of 70 mg sulfatide in 1.0 ml phosphate buffered saline to treat systemic lupus erythematsosus. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat Alzheimer's disease. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat rheumatoid arthritis. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat autoimmune hepatitis. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat celiac disease. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat insulin dependent diabetes mellitus. This dosage can be adjusted based on the results of the treatment and the judgment of the attending physician. Treatment is preferably continued for at least about 1 or 2 weeks, preferably at least about 1 or 2 months, and may be continued on a chronic basis.

In another exemplary embodiment, an 70 kg adult human is given a daily i.m. injection of 70 mg sulfatide in 1.0 ml phosphate buffered saline to treat asthma. In the alternative, the 70 kg adult human is given a daily inhalation treatment of 70 mg sulfatide for the treatment of asthma. These dosages can be adjusted based on the results of the treatment and the judgment of the attending physician. Treatment is preferably continued for at least about 1 or 2 weeks, preferably at least about 1 or 2 months, and may be continued on a chronic basis.

The following examples are provided for illustrative purposes only, and are in no way intended to limit the scope of the present embodiments.

EXAMPLE 1

Sulfatide Treatment of Chronic Experimental Autoimmune Encephalomyelitis (EAE)—C57.BL/6J Mouse Study Wild type, C57.BL/6J female mice, 6-8 week of age were immunized once subcutaneously with 200 µg of myelin oligodendrocyte glycoprotein peptide MOG35-55 emulsified in incomplete Freund's adjuvant (DIFCO) supplemented with attenuated *M. tuberculosis* (DIFCO) to 1.65 mg/ml. 0.15 µg of pertussis toxin (PTx; List Biological Laboratories, Inc.) was injected twice in 200 µl saline intraperitoneally 0 and 48 h later. Mice were observed daily for signs of EAE for 40 days. The average disease score for each group was calculated by averaging the maximum severity of all of the affected animals in the group. Disease severity was scored on a 5-point scale, as described earlier: 1, flaccid tail; 2, hind limb weakness; 3, hind limb paralysis; 4, whole body paralysis; 5, moribund or death.

In the treatment protocol, 20 µg of bovine brain sulfatide in 200 µl of PBS or vehicle was given intraperitoneally (either three times, 1 wk apart, or once as indicated) at the onset of EAE. In the prevention protocol, 20 µg of sulfatide dissolved in 200 µl PBS was given intraperitoneally at the time of EAE induction. Results shown in FIG. 1 demonstrate that treatment with sulfatide reverses ongoing chronic EAE in C57.BL/6J mice.

EXAMPLE 2

Sulfatide Treatment of Chronic and Relapsing Experimental Autoimmune Encephalomyelitis—SJL/J Mouse Study Wild type, SJL/J female mice, 6-8 week of age were immunized once subcutaneously with 75 µg of proteolipid protein peptide PLP139-151 emulsified in incomplete Freund's adjuvant (Difco, Detroit, Mich., USA) supplemented with attenuated *M. tuberculosis* (DIFCO) to 2 mg/ml. Mice were observed daily for signs of EAE for 50 days. The average disease score for each group was calculated by averaging the maximum severity of all of the affected animals in the group. Disease severity was scored on a 5-point scale, as described earlier: 1, flaccid tail; 2, hind limb weakness; 3, hind limb paralysis; 4, whole body paralysis; 5, moribund or death.

Figure 2:
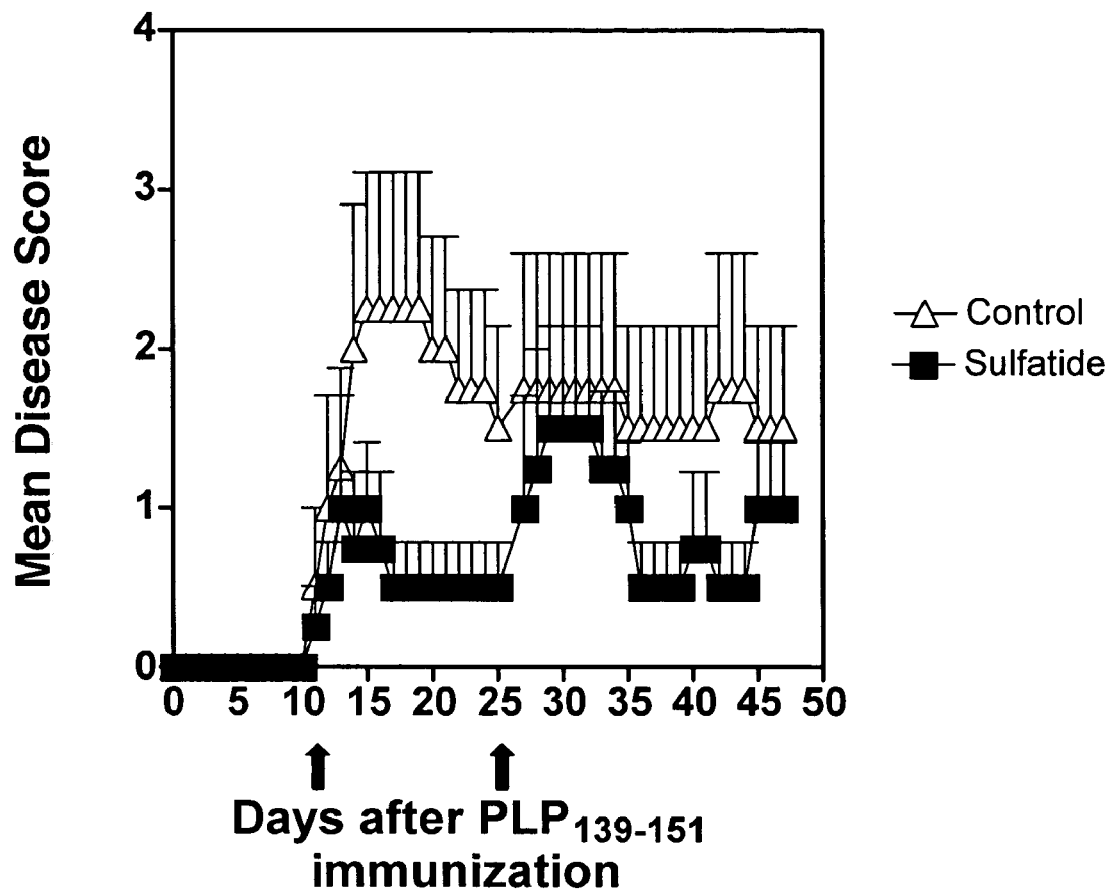
FIG. 2 shows that treatment of mice with sulfatide reverses ongoing chronic-relapsing EAE in SJL/J mice. Mice were injected intraperitoneally with 20 μg of bovine brain sulfatide (■) or with PBS/vehicle alone (Δ) at the onset of disease (left ↑) and fourteen days later (right ↑).

In the treatment protocol, 20 µg of bovine brain sulfatide in 200 µl of PBS or vehicle was given intraperitoneally at the onset of EAE and 2 weeks later. In the prevention protocol, 20 µg of sulfatide dissolved in 200 µl PBS was given intraperitoneally at the time of EAE induction. Results shown in FIG. 2 demonstrate that treatment of mice with sulfatide reverses ongoing chronic-relapsing EAE in SJL/J mice.

EXAMPLE 3

Cis-tetracosenoyl Sulfatide Treatment of Chronic and Relapsing Experimental Autoimmune Encephalomyelitis (EAE)—SJL/J Mouse Study Wild type, SJL/J female mice, 6-8 wk of age were immunized once subcutaneously with 75 µg of PLP139-151 peptide emulsified in IFA (DIFCO) supplemented with attenuated *M. tuberculosis* (DIFCO) to 2 mg/ml. Mice were observed daily for signs of EAE for 50 days. The average disease score for each group was calculated by averaging the maximum severity of all of the affected animals in the group. Disease severity was scored on a 5-point scale, as described earlier: 1, flaccid tail; 2, hind limb weakness; 3, hind limb paralysis; 4, whole body paralysis; 5, moribund or death.

Figure 3:
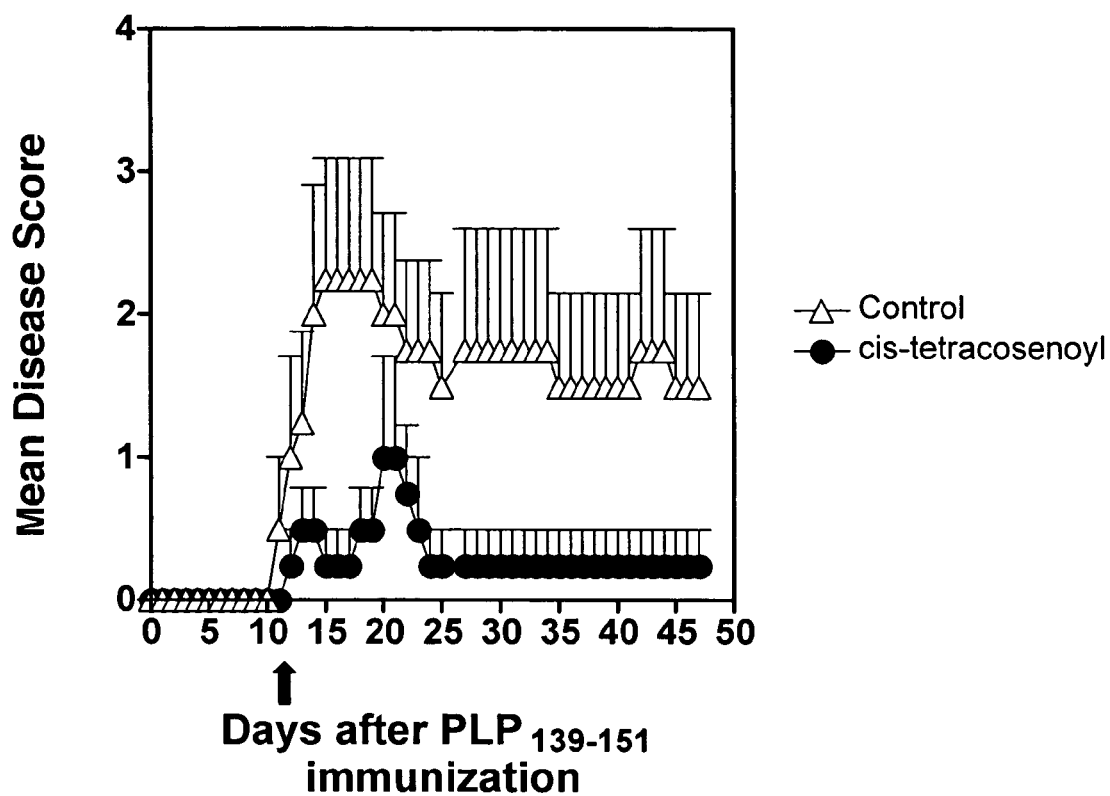
FIG. 3 shows that treatment of mice with cis-teracosenoyl sulfatide reverses ongoing chronic-relapsing EAE in SJL/J mice. Mice were injected intraperitoneally with 20 μg of cis-teracosenoyl sulfatide (●) or with PBS/vehicle alone (Δ) at the onset of disease (↑).

In the treatment protocol, 20 µg of semi-synthetic, cis-tetracosenoyl sulfatide (Formula (III)) in 200 µl of PBS or vehicle was given intraperitoneally at the onset of EAE. Results shown in FIG. 3 demonstrate that treatment of mice with cis-teracosenoyl sulfatide reverses ongoing chronic-relapsing EAE in SJL/J mice

EXAMPLE 4

Sulfatide Treatment of Diabetes—Non-Obese Diabetic or NOD Mouse Study

Figure 4:
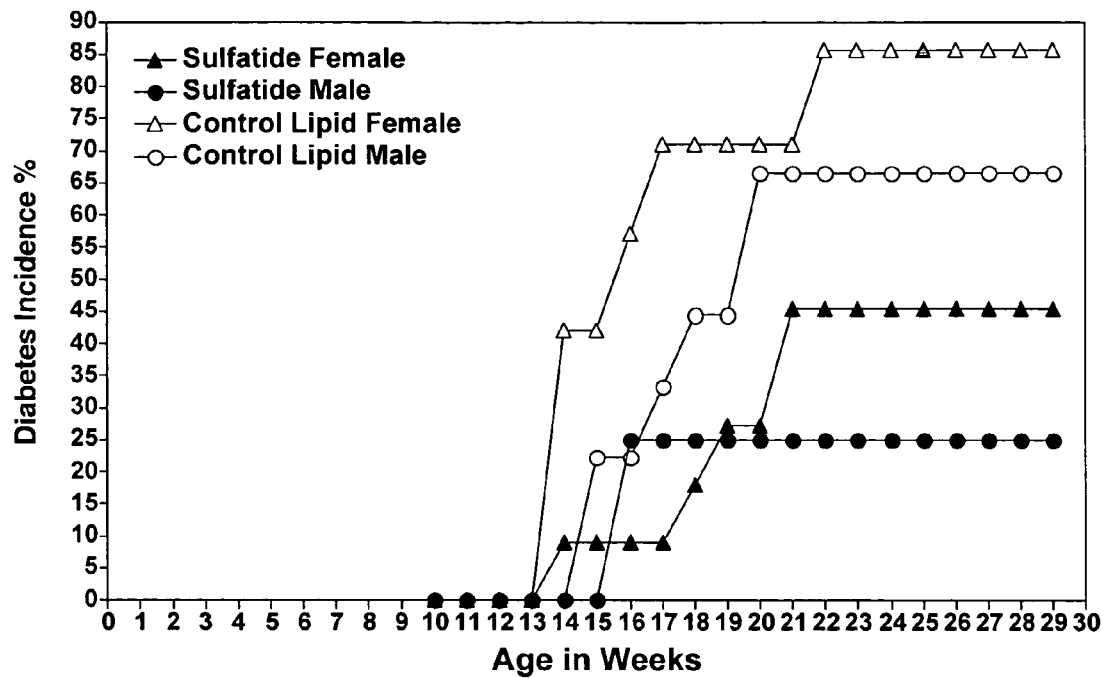
FIG. 4 shows that administration of sulfatide in nonobese diabetic (NOD) mice prevents diabetes. Female and male NOD mice were treated with bovine brain sulfatide, (○) and (●) or with control lipid (Mono GM-1), (Δ) and (○).

Groups of age-matched, 3 weeks old NOD mice (10-11 in each group) were given 3 weekly intraperitoneal injections of 20 µg bovine brain sulfatide or control lipid (Mono GM-1) in vehicle/PBS. Mice were monitored weekly for the glucose levels in urine and blood. The diabetes was diagnosed when blood glucose levels were >250 mg/dL in two consecutive readings. These data are representative of two independent experiments. Results shown in FIG. 4 demonstrate that administration of sulfatide in NOD mice prevents diabetes.

EXAMPLE 5

Liver Injury Study Following Sulfatide Treatment of Autoimmune Hepatitis

Con A model: A dose of 8.5 mg/kg of Concanavalin A (Con A) (dissolved in pyrogen free phosphate buffer saline, PBS) was injected into female C57BL/6 mice intravenously (i. v.). 20 µg (1 mg/kg/m) of bovine brain sulfatide was administered intraperitonially (i. p.) immediately after Con A injection. Control mice were injected in parallel with PBS.

The serum was collected following administration with Con A or Con A+sulfatide and kept at −20° C. until use. The serum enzymes were measured at 0, 6, 12, 24, 48 and 72 hours following Con A or Con A+ sulfatide injection. Serum levels ALT and AST were determined with the help of Laboratory Corporation of America, San Diego, Calif.

Figure 5:
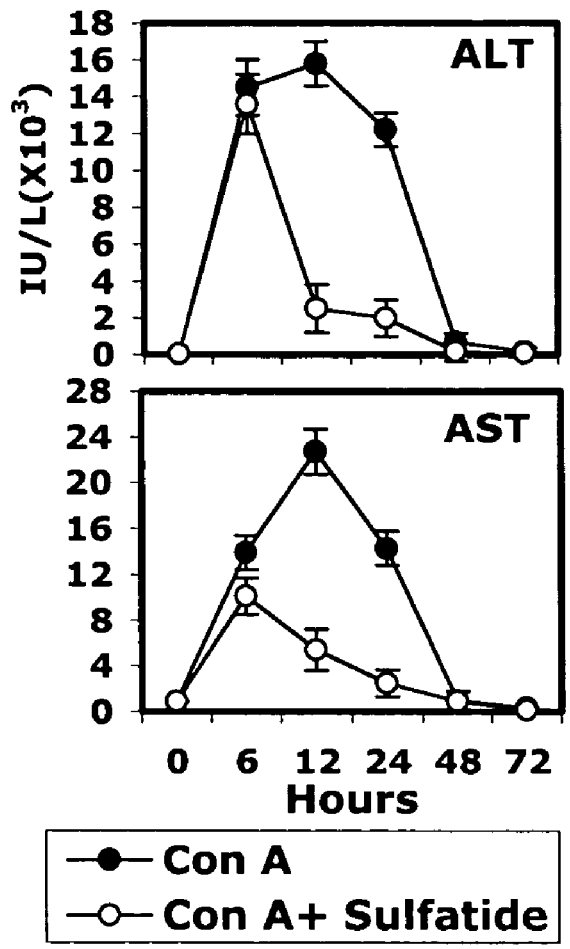
FIG. 5 shows that serum enzymes, alanine amino transferase (ALT) (top plot), and aspartate amino transferase (AST) (bottom plot) levels significantly decreased in Con A+ bovine brain sulfatide (○) injected mice in comparison to the Con A (●) injected mice.
Figure 6:
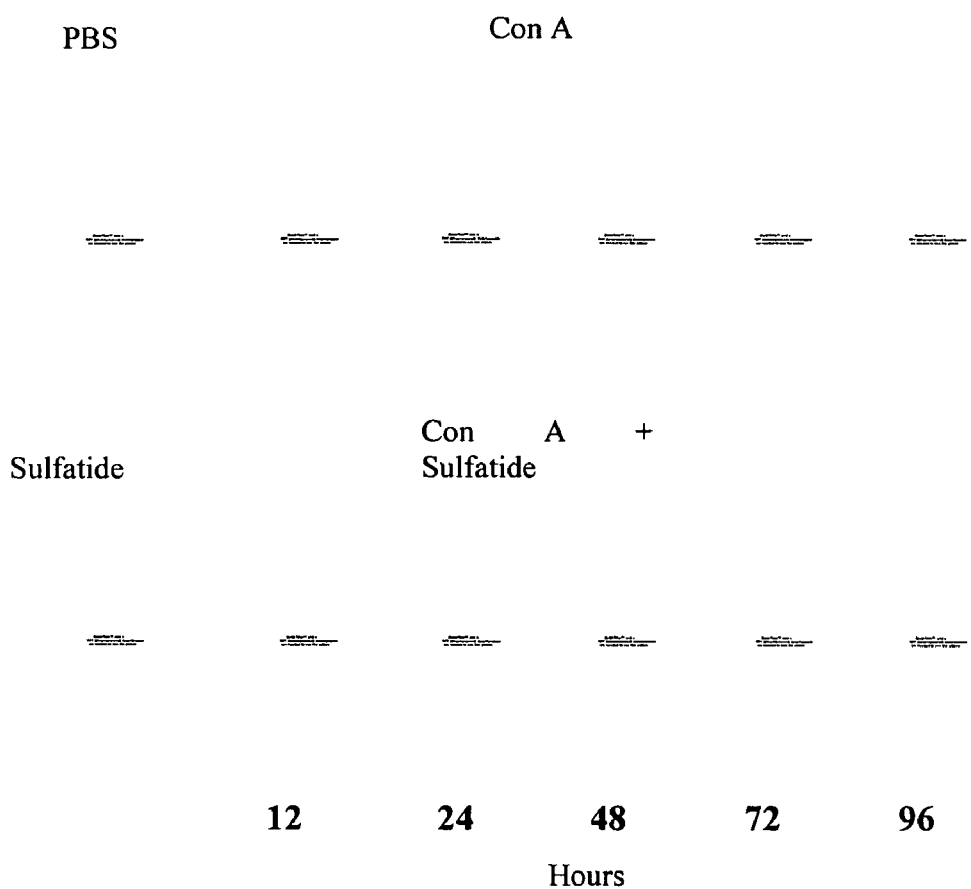
FIG. 6 shows hematoxylin and eosin stained liver sections demonstrating markedly improved hepatic histology in sulfatide-treatment mice (second panel) relative to mice in the control group (first panel) at indicated time points. Second panel includes a control liver section following only bovine brain sulfatide injection.

Comparable levels of serum enzymes, alanine amino transferase and aspartate amino transferase were observed 6 hours after Con A or Con A+ sulfatide injected mice. Con A (●) injected mice, serum ALT and AST peaked around 12 h (ALT≈15.8×10$^3$ IU/L and AST≈22.7×10$^3$ IU/L) and returned to base line by 48 hours. In contrast, following combination of Con A+ sulfatide (○) injection (FIG. 5), a significant decrease in serum level of ALT and AST (ALT≈2.5≈10$^3$ IU/L and AST≈5.4×10$^3$ IU/L) by 12 h was recorded and returned to base line by 24 h. p<0.0001 at 12 h.

EXAMPLE 6

A Dramatic Improvement in Hepatitis Induced Liver Tissue Damage in Mice Treated with Sulfatide Liver tissue was fixed in 10% formaldehyde solution at the indicated time points and kept at room temperature until use. Histological examination using hematoxylin and eosin staining was performed at Pacific Pathology Inc., San Diego, Calif.

A representative H&E-stained liver sections demonstrating markedly improved hepatic histology in Con A+ bovine brain sulfatide treatment mice relative to Con A treatment mice in the indicated time points. Histological examination showed diffuse and massive infiltration and severe necrosis at the indicated time points following Con A injection mice, top panel. In contrast, sulfatide+Con A injection was associated with mild injury in terms of less infiltration and less necrosis in the 12 h to 48 h liver sections and histology returned to normal by 72 h, bottom panel. The bottom panel, left corner liver section represented at 24 h following only sulfatide injection was a control.

EXAMPLE 7

Protection from Liver Damage from Hepatitis in Mice Injected with Sulfatide

Liver gross morphology was examined on days 3, 4 and 7 following Con A or Con A+ Sulfatide injected mice. Representative liver photographs demonstrating severe necrosis (white spot) in only Con A treated mice (middle panel) but not in Con A+ bovine brain sulfatide treated mice (lower panel) at the indicated times. Top panel shows PBS or sulfatide alone following 24 hours injection.

Figure 7:
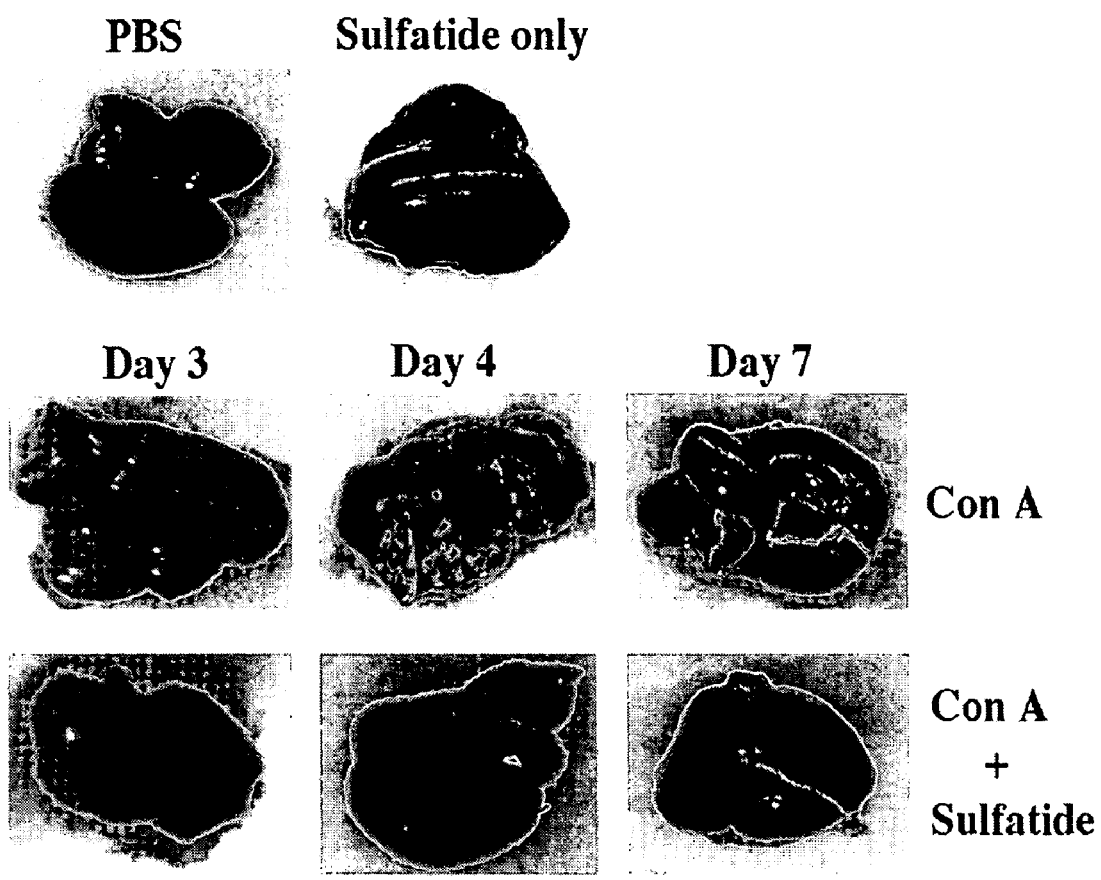
FIG. 7 shows a complete protection from gross morphological liver damage from hepatitis following sulfatide treatment. Liver morphology of Con A injected mice (second panel), Con A+ bovine brain sulfatide injected mice (third panel) and PBS or 24 hour sulfatide injected mice as control samples (first panel).

As shown in FIG. 7, a severe necrosis (white spots) was observed by macroscopic view of whole liver photographs on days 3, 4, and 7 following Con A-induced hepatitis mice. There was no liver necrosis (white spots) on days 3, 4, and 7 following a combination of Con A+ sulfatide injection (bottom panel) compared to the PBS or sulfatide (24 h) injection (top panel). These results show that co-injection with sulfatide protects against Con A-induced hepatitis.

EXAMPLE 8

Sulfatide Treatment Prevents HIV-1 Infection and Replication in SCID-hu Mice

Figure 8:
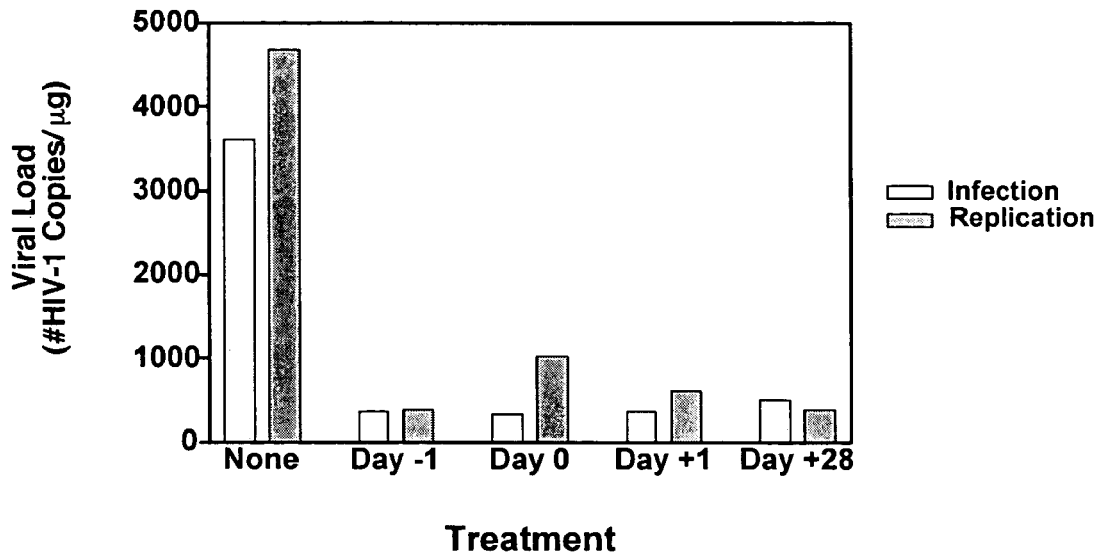
FIG. 8 shows that administration of bovine brain sulfatide in SCID-hu mice drastically lowers HIV-1 infection as well as HIV-1 replication.

Thymus/liver implants of SCID-hu mice were infected with HIV-1 virus. Mice were given 20 µg of bovine brain sulfatide (Formula I) in 200 µl of PBS, intraperitoneally, twice a week at various points of viral infection of the animals. Thymus/liver implants from these mice were extracted and HIV-1 viral load was determined, including viral infection and replication. Results shown in FIG. 8 demonstrate that administration of sulfatide in SCID-hu mice drastically lowers the HIV-1 infection as well as the HIV-1 replication.

EXAMPLE 9

Figure 9:
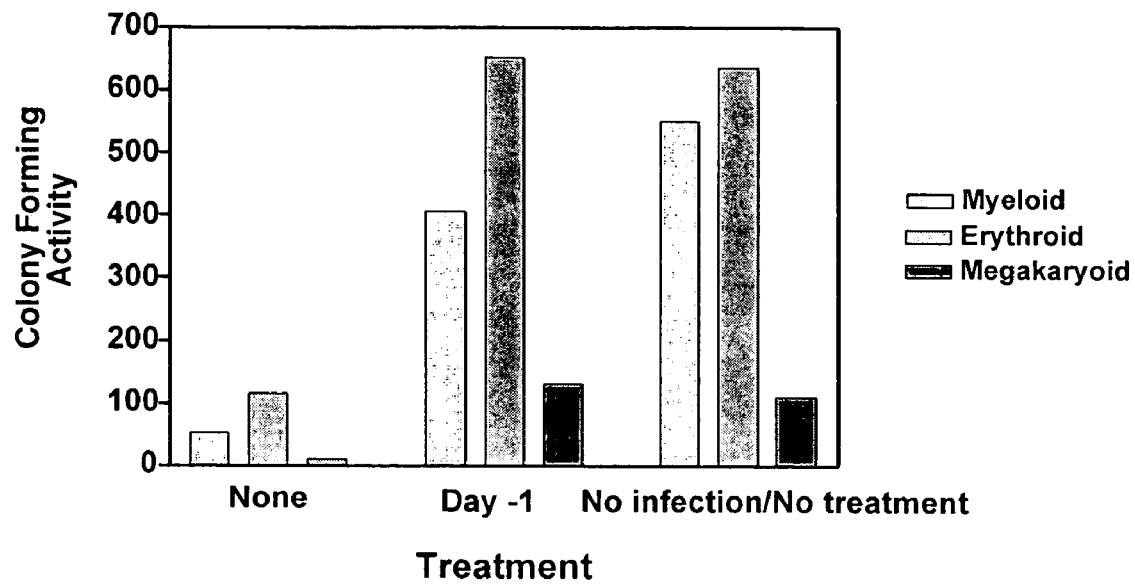
FIG. 9 shows that administration of bovine brain sulfatide in SCID-hu mice maintains the multilineage colony forming activity of human thymocytes during HIV-1 infection.

Sulfatide Treatment Restores the Thymopoetic Potential of Human Implants in SCID-hu Mice Thymus/liver implants of SCID-hu mice were infected with HIV-1 virus. Mice were given 20 µg of bovine brain sulfatide in 200 µl of PBS, intraperitoneally, twice a week at various time points in relation to the viral infection of animals. Multilineage hematopoiesis was assessed in vitro by colony forming activity of $5 \times 10^6$ total cells derived from Thy/Liv implants, in methylcellulose (myeloid and erythroid), and in megacult-C (megakaryoid) membranes. Results shown in FIG. 9 demonstrate that administration of sulfatide in SCID-hu mice maintains the multilineage colony forming activity of human thymocytes during HIV-1 infection.

EQUIVALENTS

The foregoing written specification is considered to be sufficient to enable one skilled in the art to practice the present embodiments. The foregoing description details certain preferred embodiments and describes the best mode contemplated by the inventors. It will be appreciated, however, that no matter how detailed the foregoing may appear in text, the present embodiments may be practiced in many ways and should be construed in accordance with the appended claims and any equivalents thereof.

What is claimed is:

1. A method of treating multiple sclerosis in a patient comprising administering an effective amount of a pharmaceutical composition comprising a single sulfatide component, wherein the sulfatide component consists essentially of a sulfatide having the following chemical structure:

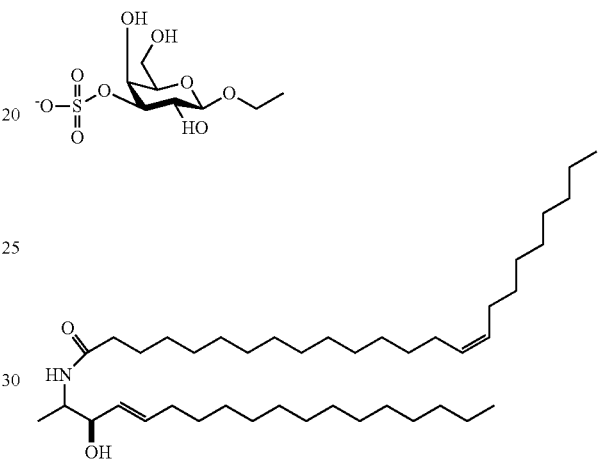

2. The method of claim 1 wherein the sulfatide inactivates iNK T cells.

3. The method of claim 1 wherein the effective amount of sulfatide is 0.1-10 mg/kg body weight.

* * * * *